United States Patent
Seul et al.

(10) Patent No.: US 10,208,347 B2
(45) Date of Patent: Feb. 19, 2019

(54) ATTRIBUTE SIEVING AND PROFILING WITH SAMPLE ENRICHMENT BY OPTIMIZED POOLING

(71) Applicant: BioInventors & Entrepreneurs Network, LLC, Warren, NJ (US)

(72) Inventors: Michael Seul, Basking Ridge, NJ (US); Ghazala Hashmi, Holmdel, NJ (US)

(73) Assignee: BioInventors & Entrepreneurs Network, LLC, Warren, NJ (US)

( * ) Notice: Subject to any disclaimer, the term of this patent is extended or adjusted under 35 U.S.C. 154(b) by 140 days.

(21) Appl. No.: 15/202,035

(22) Filed: Jul. 5, 2016

(65) Prior Publication Data

US 2017/0342489 A1  Nov. 30, 2017

Related U.S. Application Data

(60) Provisional application No. 62/341,380, filed on May 25, 2016.

(51) Int. Cl.
| | |
|---|---|
| *C12Q 1/68* | (2018.01) |
| *G01N 33/80* | (2006.01) |
| *G01N 33/569* | (2006.01) |
| *G06N 7/00* | (2006.01) |
| *C12Q 1/6881* | (2018.01) |
| *G01N 33/50* | (2006.01) |
| *G06F 19/12* | (2011.01) |

(52) U.S. Cl.
CPC ............ *C12Q 1/6881* (2013.01); *C12Q 1/68* (2013.01); *G01N 33/50* (2013.01); *G01N 33/56977* (2013.01); *G01N 33/80* (2013.01); *G06F 19/12* (2013.01); *G06N 7/005* (2013.01); *C12Q 2600/156* (2013.01); *C12Q 2600/158* (2013.01); *G01N 2333/70539* (2013.01)

(58) Field of Classification Search
CPC .. G06N 7/005; G01N 33/80; G01N 33/56977; G01N 2333/70539; C12Q 1/6881; C12Q 2600/158; C12Q 2600/156
See application file for complete search history.

(56) References Cited

U.S. PATENT DOCUMENTS

| | | | |
|---|---|---|---|
| 6,413,780 B1 * | 7/2002 | Bach | B01L 7/52 198/347.3 |
| 9,133,567 B2 | 9/2015 | Seul | |
| 2013/0029854 A1 * | 1/2013 | Seul | C40B 20/04 506/4 |
| 2015/0315568 A1 | 9/2015 | Seul | |

OTHER PUBLICATIONS

Williams, Brian G. "Optimal pooling strategies for laboratory testing." 2010, arXiv:1007.4903v1 [q-bio.QM]. arXiv.org e-Print archive. https://arxiv.org/abs/1007.4903 (accessed May 18, 2018). (Year: 2010).*
Prabhu et al., "Overlapping pools for high-throughput targeted resequencing" Genome Research 19:1254-61 (2009).
Erlich et al., "DNA Sudoku—harnessing high-throughput sequencing for multiplexed specimen analysis" Genome Research 19:1243-53 (2009).

* cited by examiner

*Primary Examiner* — Christopher Adam Hixson
(74) *Attorney, Agent, or Firm* — Eric P. Mirabel

(57) ABSTRACT

A process of identifying a plurality of biological samples having particular desired attributes by testing pooled samples and selecting, for intended uses such as transfusion, or for subsequent analysis that is thereby enriched for such samples, pooled samples which have, or may have, said desired attributes. The preferred number of samples per pool "d" is determined by selecting an integer value as d which produces the maximum or a value near the maximum of the product of: d times the expected number of unambiguous sample pools, where a sample pool is unambiguous if all of the samples have the desired attributes, and is otherwise ambiguous if at least one sample has the desired attributes. The value selected as d can be greater than the maximum product above, so as to enlarge the total number of samples assayed in determining the desired attributes.

23 Claims, 12 Drawing Sheets

| Pool size | Samples per plate | prob(no var) | | | N of unambig pools (=wells) | N of samples in unambig pools |
|---|---|---|---|---|---|---|
| | | Afa E | Afa Fya | Afa NA | | |
| d | 96 | | 0.9 | | | |
| 1 | 96 | 0.78 | 0.81 | 1.00 | 67 | 67 |
| 2 | 192 | 0.61 | 0.73 | 1.00 | 47 | 94 |
| 3 | 288 | 0.47 | 0.66 | 1.00 | 33 | 99 |
| 4 | 384 | 0.37 | 0.53 | 1.00 | 23 | 92 |
| 6 | 576 | 0.23 | 0.43 | 1.00 | 11 | 66 |
| 8 | 768 | 0.14 | 0.28 | 1.00 | 5 | 40 |
| 12 | 1152 | 0.05 | | 1.00 | 1 | 12 |

| Antigen abundances | | |
|---|---|---|
| | Cau | Afa |
| C | 68.0% | 27.0% |
| c | 80.0% | 96.0% |
| E | 29.0% | 22.0% |
| e | 98.0% | 98.0% |
| K | 9.0% | 2.0% |
| k | 99.0% | 100.0% |
| Fya | 66.0% | 10.0% |
| Fyb | 83.0% | 23.0% |
| V | 1.0% | 30.0% |
| VS | 0.0% | 30.0% |
| Jka | 77.0% | 92.0% |
| Jkb | 74.0% | 49.0% |
| M | 78.0% | 74.0% |
| N | 72.0% | 75.0% |
| S | 55.0% | 31.0% |
| s | 89.0% | 93.0% |
| NA | 0.0% | 0.0% |

FIG. 3

| S. No. | Observed Antibody Pattern | N of Antibodies in Pattern | N of Patients | N of Unambiguous 4-Pools mean | std dev | N of Samples in Unambig Pools 4 |
|---|---|---|---|---|---|---|
| 1 | --E------------------- | 1 | 32 | 42 | 5.3 | 168 |
| 2 | -------K-------------- | 1 | 11 | 94.1 | 1.1 | 376 |
| 3 | -C-------------------- | 1 | 6 | 41 | 3.8 | 164 |
| 4 | -C-------------------- | 1 | 3 |  |  | NA |
| 5 | -----------Fya-------- | 1 | 2 | 23.1 | 4.1 | 92 |
| 6 | ---------------M------ | 1 | 2 | 0 | 0 | 0 |
| 7 | --CW------------------ | 1 | 1 | 89.7 | 3.62 | 358 |
| 8 | ----------------S----- | 1 | 1 | 20.9 | 4.3 | 83 |
| 9 | -C-E------------------ | 2 | 7 | 16.3 | 2.6 | 65 |
| 10 | -E----K--------------- | 2 | 4 | 41 | 5.6 | 164 |
| 11 | -Ce------------------- | 2 | 3 | 0 | 0 | 0 |
| 12 | -E---------Jkb-------- | 2 | 2 | 3.4 | 1 | 13 |
| 13 | ------K----Fya-------- | 2 | 2 | 22.5 | 4 | 90 |
| 14 | -C-E------------------ | 2 | 2 | 16.3 | 2.6 | 65 |
| 15 | -C-------K------------ | 2 | 1 | 40 | 3.8 | 160 |
| 16 | --E--------Fya-------- | 2 | 1 | 10.2 | 3 | 40 |
| 17 | --E--------Jsa-------- | 2 | 1 | 42 | 5.3 | 168 |
| 18 | --E-------------S----- | 2 | 1 | 9.7 | 3.9 | 38 |
| 19 | --E-------------S----- | 2 | 1 |  |  | NA |
| 20 | -C-E---K-------------- | 3 | 5 | 15.8 | 2.8 | 63 |
| 21 | -C-E---K--CW---------- | 3 | 2 | 14.9 | 2.5 | 59 |
| 22 | -C-E-------Jkb-------- | 3 | 2 | 1 | 1 | 4 |
| 23 | -C-----K---Rb--------- | 3 | 2 | 3.3 | 1.3 | 13 |
| 24 | -C----CW---Fya-------- | 3 | 1 | 9.6 | 2.4 | 38 |
| 25 | -C----CW--------S----- | 3 | 1 | 8.3 | 2.9 | 33 |
| 26 | -C---------Fya-Fyb---- | 3 | 1 | 2.9 | 1.4 | 11 |
| 27 | -C-E-------Fya-------- | 3 | 1 | 4.6 | 1.1 | 18 |
| 28 | -c-E---K-------------- | 3 | 1 | 0 | 0 | 0 |
| 29 | -C-E-----------M------ | 3 | 1 | 0 | 0 | 0 |
| 30 | -C---------Rb-Fya----- | 3 | 1 | 0.9 | 1 | 3 |
| 31 | ---e---K---Fya-------- | 3 | 1 | 0 | 0 | 0 |
| 32 | --E--------Rb--M------ | 3 | 1 | 0 | 0 | 0 |

FIG. 5A

| S. No. | Observed Antibody Pattern | N of Antibodies in Pattern | N of Patients | N of Unambiguous 4-Pools | | N of Samples in Unambig Pools |
|---|---|---|---|---|---|---|
| | | | | mean | std dev | |
| 33 | -C--E--------------Jkb--Fya------ | 4 | 1 | 0.2 | 0.4 | 4 |
| 34 | -C--E-U-------------Jkb---------- | 4 | 1 | 0 | 0 | 0 |
| 35 | -C--E-----K-----Jka-------------- | 4 | 1 | 0 | 0 | 0 |
| 36 | -C--E-----K-----Jkb-------------- | 4 | 1 | 0.9 | 0.9 | 3 |
| 37 | -C--E-----K------------------S-- | 4 | 1 | 3.7 | 2.5 | 14 |
| 38 | -C--E-----K------------------s-- | 4 | 1 | 0 | 0 | 0 |
| 39 | -C-----------Jkb-Fya-M----------- | 4 | 1 | 0 | 0 | 0 |
| 40 | -C--------K-----Jkb-Fya---------- | 4 | 1 | 0.8 | 1 | 3 |
| 41 | -C--------K--------Fya-M--------- | 4 | 1 | 0 | 0 | 0 |
| 42 | -C--------K-----Jkb-------S----- | 4 | 1 | 0 | 0 | 0 |
| 43 | ----E--Jsa--------Fya-Fyb-------- | 4 | 1 | 2.7 | 1.7 | 10 |
| 44 | ----E-----K--------Fya--N-------- | 4 | 1 | 0.1 | 0.3 | 0 |
| 45 | ----E-----K--------Fya--S-------- | 4 | 1 | 2.4 | 1.6 | 9 |
| 46 | ----------------Jkb-Fya-Fyb--S--- | 4 | 1 | 0.1 | 0.3 | 0 |
| 47 | ----E-----K-----Jkb-Fya----S---- | 5 | 2 | 0 | 0 | 0 |
| 48 | ----E-----K-Jsa----Fyb----S----- | 5 | 1 | 3.2 | 2 | 12 |
| 49 | -C--E------Jsa-----Fya----S------ | 5 | 1 | 1.2 | 1.1 | 4 |
| 50 | -C--E-----------Jka--Fyb-N------ | 5 | 1 | 0 | 0 | 0 |
| 51 | -C--E-----------Jkb--N-S-- | 5 | 1 | 0 | 0 | 0 |
| 52 | -c--------K--------Fya----S------ | 5 | 1 | 0 | 0 | 0 |
| 53 | -C--E-----K-------Lua--Fya------- | 5 | 1 | 3.4 | 1.3 | 13 |
| 54 | -C--E-----K----Kpa--Jka---------- | 5 | 1 | 0 | 0 | 0 |
| 55 | -C--E-----K--------Fya----S------ | 5 | 1 | 1.2 | 1.1 | 4 |
| 56 | -C--E-----K-Jsa-----Fya---------- | 5 | 1 | 4.5 | 1.1 | 18 |
| 57 | -C-----V---K--------M-S--------- | 5 | 1 | 0 | 0 | 0 |
| 58 | -C--E-----K-Jsb-----Jkb-Fya------ | 6 | 1 | 0 | 0 | 0 |
| 59 | -C--E-----K-------Fya-M-S------ | 6 | 1 | 0 | 0 | 0 |
| 60 | -C--E-----K-Jsb-----Jkb----S------ | 6 | 1 | 0 | 0 | 0 |
| 61 | ---E-U----K---Kpa--Jka----N------ | 6 | 1 | 0 | 0 | 0 |
| 62 | -C--E--V--K-Jsa----Jka--Fya----- | 7 | 1 | 0 | 0 | 0 |
| 63 | -C-----------K--------Jkb-Fya-Fyb-M--S--- | 7 | 1 | 0 | 0 | 0 |
| 64 | -C--E-----K-Jsb-------Fya-Fyb-M--S---Yfb | 9 | 1 | 0 | 0 | 0 |

FIG. 5B

Identifying pools with "V- & VS-", "C- & V- & VS-", "E- & V- & VS-", "E- V- & VS-"

| "V- & VS-" | NP | NS for V- & VS- | "C- & V- & VS-" | NP | NS for C- & V- & VS- | "E- & V- & VS-" | NP | NS for E- & V- & VS- | Union (col 4, col 7) | NP | NS for C- & V- & VS- or E- & V- & VS- |
|---|---|---|---|---|---|---|---|---|---|---|---|
| [1] [1] 14 19 23 26 43 44 46 51 76 78 85 | [1] [1] 11 | 44 | [1] [1] 26 | [1] [1] 1 | 4 | [1] [1] 19 26 | [1] [1] 2 | 8 | [1] [1] 26 19 | [1] [1] 2 | 8 |
| [2] [1] 8 36 47 61 68 82 84 95 | [2] [1] 8 | 32 | [2] [1] 36 82 | [2] [1] 2 | 8 | [2] integer (0) | [2] [1] 0 | 0 | [2] [1] 36 82 | [2] [1] 2 | 8 |
| [3] [1] 4 14 15 20 26 35 38 61 71 | [3] [1] 9 | 36 | [3] [1] 38 61 71 | [3] [1] 3 | 12 | [3] [1] 71 | [3] [1] 1 | 4 | [3] [1] 38 61 71 | [3] [1] 3 | 12 |
| [4] [1] 16 20 32 36 39 44 53 58 72 95 | [4] [1] 10 | 40 | [4] [1] 36 39 58 | [4] [1] 3 | 12 | [4] [1] 36 58 95 | [4] [1] 3 | 12 | [4] [1] 36 39 58 95 | [4] [1] 4 | 16 |
| [5] [1] 6 16 19 20 34 35 38 42 52 57 91 | [5] [1] 11 | 44 | [5] [1] 6 19 | [5] [1] 2 | 8 | [5] [1] 19 20 35 | [5] [1] 3 | 12 | [5] [1] 6 19 20 35 | [5] [1] 4 | 16 |
| [6] [1] 12 27 35 47 58 60 63 65 | [6] [1] 8 | 32 | [6] [1] 27 | [6] [1] 1 | 4 | [6] [1] 27 60 | [6] [1] 2 | 8 | [6] [1] 27 60 | [6] [1] 2 | 8 |
| [7] [1] 3 6 20 30 34 38 56 57 61 62 71 89 | [7] [1] 12 | 48 | [7] [1] 6 30 56 89 | [7] [1] 4 | 16 | [7] [1] 6 20 57 62 | [7] [1] 4 | 16 | [7] [1] 6 30 56 89 20 57 62 | [7] [1] 7 | 28 |
| [8] [1] 2 13 19 20 31 40 45 50 72 84 93 | [8] [1] 11 | 44 | [8] [1] 13 45 50 | [8] [1] 3 | 12 | [8] [1] 2 13 19 20 50 72 | [8] [1] 6 | 24 | [8] [1] 13 45 50 2 19 20 72 | [8] [1] 7 | 28 |
| [9] [1] 9 18 24 32 60 69 70 77 94 | [9] [1] 9 | 36 | [9] [1] 94 | [9] [1] 1 | 4 | [9] [1] 9 69 70 | [9] [1] 3 | 12 | [9] [1] 94 9 69 70 | [9] [1] 4 | 16 |
| [10] [1] 16 23 28 29 30 42 68 76 | [10] [1] 8 | 32 | [10] [1] 68 76 | [10] [1] 2 | 8 | [10] [1] 23 42 | [10] [1] 2 | 8 | [10] [1] 68 76 23 42 | [10] [1] 4 | 16 |
| | | 388 | | | 88 | | | 104 | | | 152 |

NP = Number of unambigous pools
NS = Number of samples in unambiguous pools

FIG. 6

| Identifying pools with "all C- & all V- & any (=at least one) hrB-" | | | | | | |
|---|---|---|---|---|---|---|
| Phenotypes of samples in 3 pools with "all C- &V- & at least one hrB | attribute pattern>> | -C- | -E- | -V- | -VS- | -hrB- |
| > PoolSet[[1]][[c(34, 47, 84).] | | | | | | |
| [,1] | | | | | | |
| [1,] "M-N-s-S-U-c-CW-e-hrS-VS-Lub-Jsb-k-Kpb-FyNull-Jka-Dib-yta-Dob-Hy-Joa-Coa" | | 1 | 1 | 1 | | 1 |
| [2,] "M-N-s-S-U-c-e-hrB-hrS-Lub-Jsb-k-Kpb-Fya-Fyb-Jka-Dib-Yta-Dob-Hy-Joa-Coa" | | 1 | 1 | 1 | 1 | |
| [3,] "M-s-U-c-e-hrB-hrS-Vs-Lub-Jsb-k-Kpb-Fyb-Jkb-Dib-Yta-Dob-Hy-Joa-Coa" | | 1 | | 1 | 1 | |
| [,2] | | | | | | |
| [1,] "M-s-U-c-cE-e-E-hrB-hrS-Lub-Jsb-k-Kpb-Fyb-Jka-Jkb-Dib-Yta-Doa-Hy-Joa-Coa" | | 1 | 1 | 1 | 1 | |
| [2,] "N-s-U-c-e-hrB-hrS-Lub-Jsb-k-Kpb-Fyb-Jka-Dib-Yta-Doa-Dob-Hy-Joa-Coa" | | 1 | 1 | 1 | 1 | |
| [3,] "M-N-s-U-c-e-hrB-hrS-Lub-Jsb-k-Kpb-Fya-Jka-Dib-Yta-Dob-Hy-Joa-Coa" | | 1 | | 1 | 1 | |
| [,3] | | | | | | |
| [1,] "M-s-U-c-cE-e-hrB-hrS-Lub-Jsb-k-Kpb-Fya-Jka-Dib-Yta-Dob-Hy-Joa-Coa" | | 1 | 1 | 1 | 1 | |
| [2,] "M-s-U-c-e-hrB-hrS-VS-Lub-Jsb-k-Kpb-Fya-Fyb-Jka-Dib-Yta-Doa-Dob-Hy-Joa-Coa" | | 1 | 1 | 1 | | |
| [3,] "M-s-U-c-cE-e-E-hrS-VS-Lub-Jsb-k-Kpb-Fya-Jkb-Dib-Yta-Doa-Dob-Hy-Joa-Coa" | | 1 | 1 | 1 | | 1 |
| [,4] | | | | | | |
| [1,] "M-N-s-S-U-c-CE-e-E-hrS-hrB-Lub-Jsb-k-Kpb-FyNull-Jka-Jkb-Dib-yta-Doa-Dob-Hy-Joa-Coa" | | 1 | 1 | 1 | 1 | |
| [2,] "M-N-s-S-U-c-e-hrS-Vs-Lub-Jsb-k-Kpb-FyNull-Jka-Dib-Yta-Dob-Hy-Joa-Coa" | | 1 | 1 | 1 | 1 | 1 |
| [3,] "M-s-U-c-e-hrB-Lub-Jsb-k-Kpb-Fya-Jkb-Dib-Yta-Doa-Dob-Hy-Joa-Coa" | | 1 | | 1 | 1 | |

FIG. 7

ATTRIBUTE SIEVING AND PROFILING WITH SAMPLE ENRICHMENT BY OPTIMIZED POOLING

BACKGROUND

Many clinical applications call for stratification of patients by molecular (and/or other) attributes. For example, to develop or administer personalized therapies, patients may be selected for clinical trials or drug development programs in accordance with molecular attribute profiles that provide a differential diagnosis, such as for many cancers, or indicate the efficacy and/or safety of therapy (see e.g. Doehner2010, Kurose2012).

Further, many patients with cytopenias require regular transfusion. For example, patients with anemia caused by renal disease, or by hematologic disorders including leukemia, sickle cell anemia, or thalassemia, require regular red blood cell transfusions, and especially the care for the chronically transfusion-dependent generates substantial cost (Wayne2000). Likewise, patients with certain hematologic disorders including acute leukemias and certain cases of myelodysplatic syndrome who develop thrombocytopenia require extensive platelet transfusion support, once again at substantial expense (Meehan2000). Periodic transfusion often leads to progressive alloimmunization against an increasing number of antigenic determinants displayed on the donor cells, be they red cells (Castro2002) or platelets (TRAP1997).

Platelets: Human Leukocyte Antigens ("HLA") Class I, Human Platelet Antigens ("HPA")—Patients receiving therapy for hematologic malignancies consume more than 40% of the approximately 2.1 million single donor units (or equivalents) collected in the US as of 2013 (AABB2013). Many patients have antibodies, formed in response to prior allogeneic exposure during pregnancy or previous transfusion, and others develop antibodies during treatment, and these antibodies mediate the accelerated clearance of transfused cells, leading to a poor response to transfusion and excess platelet consumption as well as excess utilization of clinical services, and extended in-hospital stays, especially for patients who respond to transfusion (Meehan2000).

In part, this state of affairs reflects the logistical difficulty of identifying suitable platelet donors quickly in view of the short expiration dating for platelets. Random searches that identify prospective donors by a negative serological crossmatch, are time-consuming and, at best, will exclude as unsuitable only those prospective donors with cognate epitopes to existing antibodies, but will not identify alloepitopes that may lead to the formation of new antibodies. The genotyping of HLA, though long since a standard approach to matching stem cell recipients and donors, as currently practiced, is complex and slow, and the prevailing strategy of procuring stem cells has been to maintain large registries of volunteers who are genotyped at registration, an expensive propositions the vast majority of these volunteers will never called. Creating large registries of potential platelet donors clearly is impractical for the routine procurement of suitable platelets, given the large demand, and the time constraints imposed by the platelet expiration dating.

Red Blood Cells: Human Erythrocyte Antigens ("HEA")—For sickle cell patients, stroke is a major risk factor, and timely (hence chronic) transfusion has been shown to be very effective in reducing that risk (eg. Lee2006). The commercial introduction of routine genotyping into donor centers and hospital transfusion services, a decade ago (Hashmi2005, Hashmi2007, Moulds2011), has greatly facilitated the procurement of suitable red cells especially for transfusion-dependent patients with multiple antibodies, a common side effect of chronic transfusion of sickle cell anemia and thalassemia patients (Castro2002, Pham2011, Chou2013). However, notwithstanding its commercial availability in several formats, genotyping, given its perceived high cost and complexity—which may require special training and in some cases certification—has been limited, in practice, to special situations that are not readily handled by serology. Serology, largely automated, has otherwise remained the "work horse" in the pre-transfusion setting, especially for large-scale "pre-selection" of candidate donors.

Finding candidate cells with desirable molecular attributes, usually in the form of a set of cell surface markers (expressed or not expressed), or a set of antigenic determinants associated with antigens such as HLA, is a search problem. The prevalent format of genotyping represents a "brute force" solution that is ill-suited to scale up. Thus, to identify, in accordance with this format, donors who do not express the RBC antigens E, V and Fya, say, one first genotypes all candidate donors at hand—one at a time—for an entire set of alleles (as in, say, BioArray Solutions' "HEA PreciseType" test, see website at Immucor, Inc.), then looks for instances, if any, that lack the specified antigens. As this attribute pattern—"E- & V- & Fya-"—is not a common one, many of the genotype determinations will be of no value, and unless they address other instances of pending requests, the investment made in those determinations may be lost.

Consequently, to reduce genotyping expenditures, many hospital transfusion services supporting transfusion-dependent patients have resorted to extraordinary measures such as pairing individual patients with special ("buddy") donors on whose continuing kindness they count for a vital part of their patient care; all the while generating tens of thousands of dollars in annual expenses for other aspects of care for the very same patients, particularly laboratory charges and "spend" for iron chelators (Wayne2000).

In the hematology/oncology setting, the situation is worse. Unless patients become non-responsive to platelet transfusion, the procurement and selection of platelets, in order to ensure hemostasis and to maintain vascular integrity, remains largely uninformed by concerns about the risk of allogeneic exposure to antigens displayed on platelets, notably HLA (class I) and HPA, and its clinical and financial consequences On the supply side, many practitioners rely on serological methods, preferably in an automated format, to "pre-screen" candidate units for genotyping, usually representing a fraction of no more than a few percent. However, for all but the most common red cell antigens such as C, E and K, this approach must rely on a limited (and expensive) supply of reagents. In addition, it has the disadvantage that it not only proceeds one sample at a time, but also one antigen at a time, and therefore requires elaborate sample handling and tracking. In the alternative, many practitioners, in lieu of extensive pre-screening, invoke simple heuristics for pre-selection, for example, on the basis of major blood type and/or declared ethnic background. Many also favor repeat donors, thereby in some cases severely narrowing the distribution of available antigen profiles.

To overcome the limitations of current approaches to large-scale genotyping generally, and to the routine procurement of blood cells or other cells with specific antigen and genotype profiles, a process is needed that: (i) enables the effective scale-up of genotyping to survey and profile large numbers of samples, and (ii) does so in a manner ensuring superior performance over the prevailing "brute-force" search strategy, preferably while decreasing, and certainly without unduly increasing, the cost per "hit". An effective search process, related to "Nucleic Acid Sieving" (U.S. Pat. No. 8,932,989 and US Publ'n No. 2015/0315568), "Allele Profiling" (US Publ'n Nos. 20130029857 and 2015/0376693) and "Attribute Profiling" (U.S. Pat. No. 9,133,567), all of which are incorporated by reference, is disclosed herein.

SUMMARY

The new process achieves its effectiveness and scalability by inspection of sample pools formed, as disclosed herein, in a manner reflecting expected abundances of desired and/or designated sample attributes, wherein the attributes preferably are molecular attributes including: alleles or haplotypes; cell surface markers, including antigens, and especially antigens or epitopes recognized by antibodies, including those previously identified in intended recipients of red blood cells or other cells. Desired attributes (aka "attributes of interest", "attribute configuration", "attribute set", "attribute pattern") may or may not be directly detectable by the testing method employed, so the process also can be effected by monitoring/testing for certain detectable attributes whose presence or absence correlates with the presence or absence of desired or detectable attributes, as in the case of an attribute pattern comprising antigens whose presence or absence correlates with the presence or absence of the alleles encoding those antigens.

The preferred embodiment includes two stages, namely:
1. A pool analysis and sample selection and enrichment (aka "sieving", "panning") stage comprising the concurrent determination of multiple attribute patterns for pooled samples, and the selection of pools on the basis of one or more criteria (aka "policies"), as illustrated in the Examples.
2. A profiling stage, for a selected subset of samples from unambiguous or ambiguous pools, comprising the determination of any additional attributes, and the resolution of any ambiguities remaining after the sieving stage.

The process includes forming pools and optionally pooled pools. Prior to sieving, aliquots from "d" samples are pooled, such that any sample of interest will be added to at least one pool and pools are unique; "d" is determined as a positive integer value that maximizes, or approximately maximizes, the expected number of samples in pools whose constituent samples are identical with respect to designated attributes, or a designated attribute set. There is an upper limit, $d_{max}$, on the total number d of samples per pool, where $d_{max}$ is based on, among other things, the ability of the assay or testing technology to detect attributes or alleles at $d_{max}$-fold dilution.

The process may further include associating all samples in pooled pools with a particular pool, as well as identifying samples having particular attributes, preferably by forming, for each pool or pooled pool, attribute-specific, source-tagged reaction products wherein each such reaction product has a source tag identifying the pool and a marker-tag identifying the attribute, as described, e.g., in U.S. Pat. No. 8,932,989 and other references in the Background section.

While many of the illustrative examples invoke the case of red blood cell ("RBC") antigens (aka "HEA"), the process and methods apply equally to selection by attribute patterns comprising other cell surface markers (e.g., platelet antigens HPA, or HLA), or other molecular attributes encoded by a set of known alleles (e.g. those for enzyme mutations or receptor polymorphisms), as well as to sample selection by allele patterns.

A pool is said to be unambiguous for a desired attribute pattern if its constituent samples are identical with respect to that attribute pattern. For unambiguous pools, the analysis can stop after the first stage with the selection of the constituent samples for the designated or other desired attributes, as illustrated herein, or can be continued, for some or all of the constituent samples, in order to determine additional attributes that may not be shared by all the constituent samples. A pool is said to be ambiguous for a desired attribute pattern if its constituent samples are not identical with respect to that attribute pattern, but at least one constituent sample has, or may have, that attribute pattern. Analysis generally must be continued to determine whether, and if so which, sample or samples in the pool have the pattern.

The determination of attributes at stage 1 or stage 2 above can be made by methods of DNA analysis to determine alleles (by, for example, sequencing or allele specific amplification or other standard methods of nucleic acid analysis) and to predict expressed antigens, or directly by standard methods of immunophenotyping, to determine antigen type and/or by serology, to establish cross-reactivity between donor cells and prospective recipient serum.

Especially in the context of allocating suitable red blood cells to transfusion-dependent patients, reliance on serological methods and processes for the pre-selection step or otherwise has several disadvantages that are overcome by DNA analysis in accordance with the process disclosed herein. First, serological reagents for many red cell antigens (e.g. V, VS, Hy, Joa) are in short supply, or unavailable for routine use. Second, the use of serological reagents for identifying the important RHCE antigens C, c, E and e has been amply demonstrated to be unreliable when encountering RHCE variants, with serious adverse clinical consequences for transfusion-dependent patients (Pham2011, Chou2013). The principal advantage of the new process is its capacity for rapidly sampling a substantially larger fraction of candidate donors, for a far larger number of attributes, than that accessible to even fully automated serological "screening", which generally proceeds one sample at a time, one antigen at a time.

The new process quickly and readily identifies samples with a number of desired attributes. The selection of samples, by matching partial profiles determined in the sieving step to desired attribute patterns, enriches—and the "de-"selection of samples not having desired attribute patterns depletes—the set of samples committed to a subsequent profiling step, thereby optimizing the benefit of additional analysis. Thus, an advantage of the process disclosed herein is: multiple rare variants are monitored simultaneously, while concurrently ensuring enrichment by pre-selection for yet additional attribute patterns.

Where, as in the preferred embodiment, both sieving and profiling steps are performed by genotyping, the profiling step, performed for selected samples, will confirm the partial profiles determined in the sieving step.

In a preferred embodiment, the classification and pre-selection, by "sieving", serves to "tune" the composition of the sample sets selected for profiling in accordance with attribute patterns reflecting pending or anticipated demand. In particular, rare configurations are more likely to be detected when including 384 samples in the initial "funnel", for example in 96 pools of 4 samples each, as compared to randomly selecting sets of 96 samples.

BRIEF DESCRIPTION OF THE DRAWINGS

FIG. 3 is a table illustrating the determination of "d", for the attribute pattern "E- & Fya-", using phenotype frequencies for African Americans (Reid2004); column 3 holds the values for the probability that all d samples are "C-", column 4 those that all samples are "Fya-". Notation: "Cau" denotes Caucasian; "Afa" denotes African Black; "NA" signifies a field to accommodate an additional marker; "Nof" is short for "Number of".

FIGS. 5A and 5B are respectively, first and second sections of a table reporting results of matching requests for sickle cell anemia patients with observed patterns of antibodies to red blood cell antigens (in accordance with Table 1 in Castro 2002) with "antigen-negative" candidate donor cells selected from unambiguous pools. For each unique observed antibody pattern, shown in the left-most column, the right-most column reports the expected number of samples found in 4-sample pools (that is: d=4) that were unambiguous with respect to that pattern, assuming phenotype frequencies for African American candidate donors (without consideration of "ABO/RhD" type); "mean" and "standard deviation" were computed for 10 replicates of 96simulated 4-sample pools. Entries of "0", in the right-most column, indicate that no unambiguous pool was identified in the 10*96 pools.

FIG. 6 is a table illustrating selections of samples from 4-sample pools identified as unambiguous for attribute configurations "V- & VS-", "C- & V- & VS-" and "E- & V- & VS-"

FIG. 7 is a table illustrating selections of samples from three 4-sample pools identified, by mixed "all" and "any" queries, as ambiguous for attribute configurations "all C- & all V- and any hrB-". Profiling of the samples in these three pools would reveal the displayed phenotypes which indicate that: sample 1 in pool 1, sample 3 in pool 3 and sample 2 in pool 4, in addition to being "C- & V-", as specified, also are "hrB-", and in fact the first and the last of these samples also are "E-."

DETAILED DESCRIPTION

Figure 1:
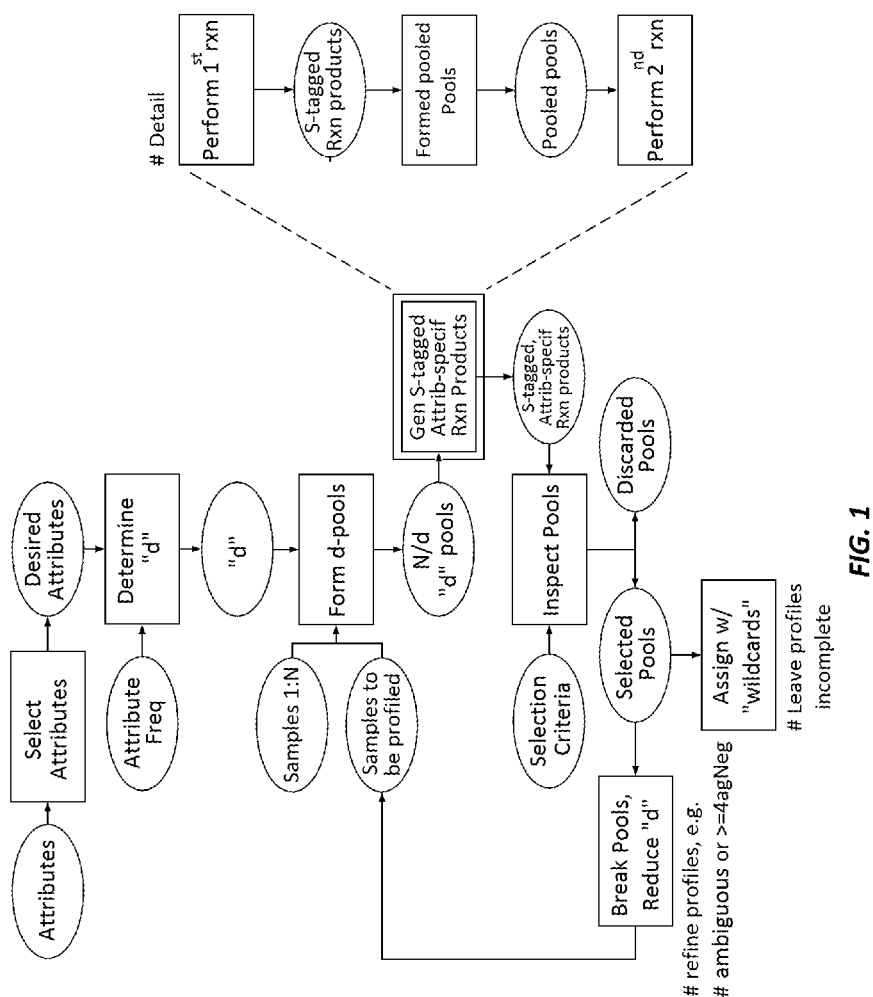
FIG. 1 is a process flow chart showing the steps in the process of attribute profiling with pooling as described herein.
Figure 2:
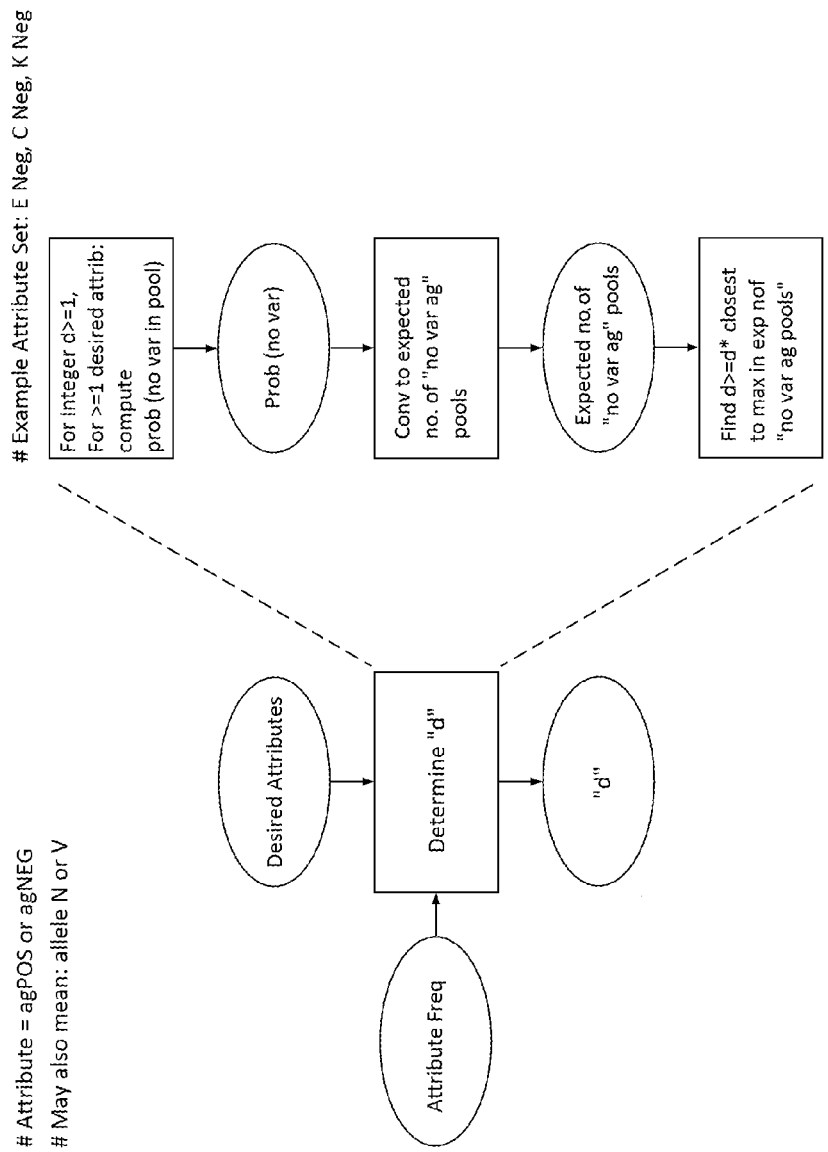
FIG. 2 is a flow chart showing how to determine "d" of FIG. 1.
Figure 4:
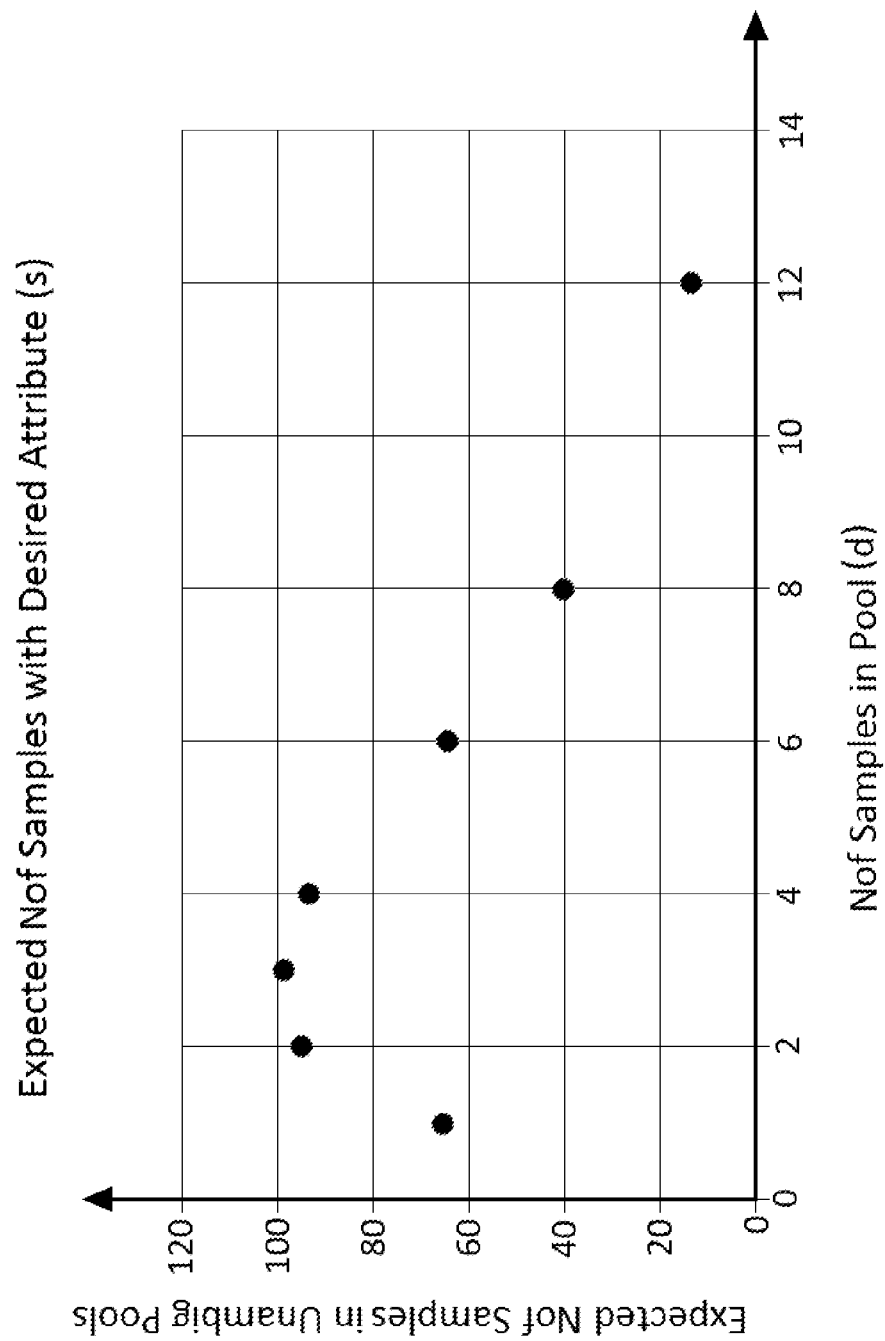
FIG. 4 is a plot of the expected number of samples in pools unambiguous with respect to "E- & Fya-" (right-most column in the left-hand Table of FIG. 3) vs "d", the number of samples per pool (left-most column of the left-hand Table of FIG. 3). The plot displays a maximum at d=3.

Referring to FIG. 1, the first process steps are: selecting desired and designated desired attributes, and based on the frequencies of the designated attributes in the population, determining the preferred or optimized number, "d", of samples per pool; FIGS. 2 to 4 more particularly illustrate applying the algorithm for determining "d". Next, sample pools are formed from a total of N samples, generally with "d" samples in each pool, resulting in N/d pools, where N preferably is chosen to produce an integer for N/d. Samples, or sample-derived products in the pools are then source-tagged ("S-tagged") to indicate their pool of origin, for identification of that pool of origin in pooled pools that may be formed in further steps, as shown in the far right of FIG. 1, prior to forming attribute-specific source-tagged second reaction products. The attributes of interest displayed by S-tagged products are attribute-tagged, where the attribute tagging preferably uses a fluorescent or other color tag or sequence tag, and where the attribute-tag identifies antigens or alleles, as described in detail in the references which are incorporated by reference in the Background section. Samples placed into sample pools may be obtained from sources including: whole blood (comprising circulating blood cells); lysates produced from buccal swabs (comprising epithelial cells) or saliva; or purified genomic DNA extracted from nucleated cells. The next step is to establish selection criteria for the S-tagged attribute-specific reaction products in the pools or pooled pools (see Examples below), where the selection criteria can refer to, e.g., all of a particular set of attributes of interest, or combinations of any such attributes. Pools with the desired attributes are selected, and other pools are discarded. Among selected pools may be pools that are unambiguous for the desired attributes, so that, even at this stage, the attribute profile of all constituent samples is known at all the positions corresponding to these attributes. Optionally, the attribute profiles of samples in unambiguous pools can be left incomplete (assigning "wildcards" to positions left undetermined, as in FIG. 1), or the samples may be individually profiled. Among selected pools also may be pools that are ambiguous for the desired attribute(s), that is, they contain attribute-specific reaction products having the desired attribute(s), as well as others that do not; for example, pools which show both the color tag(s) associated with a normal as well as the color tag(s) associated with a corresponding variant allele. In such a situation, ambiguity arises as it is unknown which of the samples in such pools have, or may have, the desired attribute(s), and which do not. To eliminate (or reduce) ambiguities, samples in ambiguous pools can be separately assayed (or first assayed in groups, to save time) for the attribute-specific properties of interest.

FIG. 2 illustrates determining "d", given desired attributes and their frequency in the population of interest. In this case, the desired attribute(s) can mean the presence or absence of an antigen, or antigen combinations, or the presence of normal ("N") or variant ("V") alleles. In FIG. 2, the desired attribute is: "negative for red blood cell antigens E and Fya.", denoted by "E- & Fya-" (short-hand for "all E- & all Fya-").

To determine the preferred "d", determine the probability, as a function of increasing positive integer values of "d", that all samples in a pool of d samples (aka d-sample pool) have the attribute pattern of interest (which may mean having the attributes in the pattern, or lacking them); in this case, this is the probability that all samples lack the antigens E and Fya. Multiply that probability by the anticipated number of pools to be formed, to obtain the expected number of pools with "no variant attribute", and multiply that number by "d" to obtain the corresponding expected number of samples in such unambiguous pools. This number will display a maximum, at some value of "d", because, as "d" increases, the number of samples per pool increases, but the expected number of pools remaining free of at least one variant decreases. This is shown in the table in FIG. 3: for increasing values of "d", in the left-most column, the right-most column records the expected number of samples in d-sample pools that are unambiguous with respect to the pattern "E- & Fya". FIG. 4 is a related plot which displays a maximum at d=3. Thus, the position of the maximum, and the optimal value of "d", may be determined from this table or the corresponding plot.

To summarize, with reference to the table in FIG. 3, determine "d" as follows. Given an attribute pattern, and the frequencies of the constituent attributes, compute, the probability that all "d" samples have that attribute (where having the attribute can mean expressing certain antigens, or NOT expressing certain antigens, as in the table in FIG. 3). Thus, for the attribute pattern "E- & Fya-", that is: "E negative and Fya negative", with respective abundances $F_E=22\%$ (that is: 22% of individuals express the antigen E and thus have the phenotype E positive) and $F_{Fya}=10\%$, as reported for African Americans (Reid2004), the probability that a sample will be E negative AND Fya negative is $(1-F_E)*(1-F_{Fya})$, and the probability that all samples in a pool of d-samples will have that attribute pattern is $\text{prob}(d)=(1-F_E)^{d}*(1-F_{Fya})^{d}$. When referring to the frequencies of the encoding alleles (here comprising the 2-valued single nucleotide polymorphisms RH676G>C and FY125A>G), rather than to phenotype frequencies, the corresponding probability, for co-dominant expression of pairs of alleles in Hardy-Weinberg equilibrium, is $(1-f_{RH676C})^{2*d}*(1-f_{FY125A})^{2*d}$.

Thus, to obtain the expected number of pools, among n such pools, multiply that probability by n, say 96; to obtain the expected number of samples in unambiguous pools, multiply that probability by d*96: this number displays a maximum at some value of "d", here at d=3 (FIGS. 3, 4). Set the desired "d" to a positive integer value at or near the position of the maximum, for example d=4: at the cost of a minor decrease in the maximum value of expected samples in unambiguous pools (i.e., 96 at d=3 vs 92 at d=4) selecting the larger d-value permits us to survey a larger number of initial samples, d*96. Further, combining samples in accordance with powers of 2 has certain practical advantages in the laboratory as it facilitates adoption of recursive processes for making pools, e.g. "pair samples", then "pair pairs of samples" and so on.

The process accommodates two or more designated attribute patterns of interest, as follows. For each such attribute pattern, determine the preferred "d" as described; if these first and second preferred values of "d", say "d1" and "d2" differ, and especially if they differ substantially, d1>>d2, say, prepare two sets of pools accordingly, one with pools comprising "d1" samples each, the other with pools comprising "d2" samples each, and perform the "sieving" step for each pool set, in parallel or in series. In the former case, the "d2"-pools may hold samples randomly selected from those placed into the "d1"-pools or may comprise a separate set of samples; in the latter case, pools placed into the "d2"-pools may be enriched by samples selected from selected "d1"-pools.

EXAMPLES

Simulation of Antigen Profiles in Random 4-Sample Pools—A set of 96 pools, each comprising d=4 samples was generated, each of the samples represented by a phenotype constructed by randomly selecting pairs of alleles encoding the principal antigens associated with the RBC blood groups MNS, RH, LU ("Lutheran"), KEL ("Kell"), FY ("Duffy"), JK ("Kidd"), DI ("Diego"), YT ("Cartwright"), DO ("Dombrock") and CO ("Colton") (Reid 2004). Allele frequencies were determined by analysis of experimental genotype data for African Americans in the Southern United States. For illustration, a pool comprising a set of four phenotypes is as follows:

[1]   "M-s-U-c-e-hrB-hrS-Lub-Jsb-k-Kpb-Fya-Jka-Jkb-Dib-Yta-Dob-Hy-Joa-Coa"
[2]   "M-N-s-S-U-c-CW-e-hrB-hrS-Lub-Jsb-k-Kpb-Fya-Jka-Jkb-Dib-Yta-Doa-Hy-Joa-Coa"
[3]   "M-s-S-U-c-e-hrB-hrS-Lub-Jsb-k-Kpb-Fya-Jka-Jkb-Dib-Yta-Dob-Hy-Joa-Coa"
[4]   "M-s-U-c-e-hrB-hrS-Lub-Jsb-k-Kpb-FyNull-Jkb-Dib-Yta-Doa-Dob-Hy-Joa-Coa"

The information from this simulation was used in generating the information in several of the examples below.

"All" Queries (See Also Below)—These queries identify pools where all samples are identical with respect to the specified attribute pattern, e.g.: identify pools wherein ALL samples lack the antigens C, E and K: "C- & E- & K-" (short for "all C- & all E- & all K-"); or "C- & E- & CW-"; or "E- & Fya- & Jkb-", etc.; pools identified by such "all" queries are said to be "unambiguous" with respect to the specified attribute pattern.

Filling Requests by Selecting Donor Units from Unambiguous Pools: Sieving Only—The table in FIG. 5 reports allo-antibody combinations observed in transfusion-dependent sickle cell anemia patients (extracted from Table 1 in Castro2002). Transfusion support for these patients calls for the procurement of "antigen-negative" units, that is: units that do not expose patients with allo-antibodies to cognate antigens. "All" queries, against 10 sets of 96 four-sample pools generated by simulation, return, for attribute patterns comprising the set of cognate antigens for each of the observed antibody combinations in the second column off the table in FIG. 5, the number of pools determined to be unambiguous for that combination: the mean over 10 replicates, and the corresponding standard deviation are shown along with the expected number of samples in unambiguous pools, in the right-most column. Thus, unambiguous pools would yield, without the need for further analysis, suitable samples for 103 of the 135 patients included in the compilation (though total consumption, not provided in Castro2002, may be expected to vary from patient-to-patient); this specifically includes most patients with up to 3 antibodies, and many of those with up to 5 antibodies. In addition, the set of samples selected for further analysis may be enriched by samples with specific partial attribute profiles. In many cases, pools selected as unambiguous for a designated attribute pattern, also are unambiguous with respect to additional attributes of potential interest. For example, in 10 sets of 96 four-sample pools, those selected as unambiguous with respect to "C- & K- & Jsa- & Fyb- & S-", on average 4.4 (+/−1.79) pools, also were unambiguous for "Dia- & Cob- & Ytb- & Joa+& hrS+", and all but 3 (of 44) pools, in addition, were unambiguous for "CW- & CX-", while 18 were unambiguous for "M+", so that, for a small number of pools, even the MNS antigens were determined without the further analysis. Thus, sieving alone furnishes a considerable amount of information, even for complex desired attribute patterns.

Sample Allocation Policy—The pools identified in the table in FIG. 5 as unambiguous for the absence of antigens targeted by antibodies commonly observed in sickle cell patients are overlapping pools. That is, the same pool may be unambiguous for more than one of these attribute patterns of interest, and this calls for an allocation strategy to determine which of two or more desired attribute patterns will govern the selection of samples from specific qualifying pools. Generally, the more challenging an attribute pattern, the smaller the expected number of suitable candidate samples, suggesting a first allocation strategy in accordance with this greedy heuristic: select samples for the most challenging attribute pattern first. Here, challenging attribute patterns are those producing a high probability of an ambiguity (thereby reducing the expected number of pools remaining free of ambiguities); thus, the larger the number attributes in a pattern, or the more polymorphic an allele encoding antithetical antigens, say, the more challenging the pattern comprising those attributes. For example, with reference to the table in FIG. 5, having identified, in a simulated set of 96 four-sample pools comprising red cell phenotypes, pools 7,42,44,48,89 and 95 as unambiguous for "C- & E- & Fya-", pools 48 and 89 as unambiguous for "C- & E- & K- & Fya- & S-" and pools 7,40 and 95 as unambiguous for "C- & Fya- & Fyb-", then, from the larger pool set, samples in pools 7 and 95 would be allocated to recipients having antibodies to "C, Fya, Fyb"; samples in pools 48 and 89 to recipients having antibodies to "C, E, K, Fya, S" and samples in the remaining pools 42 and 44 to recipients having antibodies (only) to "C, E, Fya". Many alternative heuristics may be invoked to guide the allocation of samples or selection of qualifying pools.

Ignoring Certain Antithetical Antigens—The selection of candidate donor samples may be guided by the antigen profile of intended recipients; for example, selection may be in accordance with combinations of known antibodies, as in the table in FIG. 5 In the case of certain antithetical antigens, if a recipient expressed both antithetical antigens, reflecting heterozygosity for the encoding alleles, then, no harm is done regardless of the values of any candidate donor sample at these antithetical antigen positions within a molecular attribute profile, that is: whether the donor sample is heterozygous or homozygous makes no difference, and such attributes can safely be ignored in selecting suitable donor samples.

"Any" ("At Least One") Queries—These queries identify pools comprising at least one sample having (or not having) the specified attribute pattern; for example, to identify all pools wherein at least one sample lacks the antigen "c": "any c-"; or "any e-", or "any hrB- & hrS-" or "any Lua+"; "any" queries may be combined with "all" queries, e.g.: "all C- & all E- & all K-" & any 5-"; or" all C- & all K- & all Fya- & any e-" & any S-". Pools identified by "any" queries are said to be ambiguous for the specified attribute(s); an example is as follows.

Identifying Uncommon Antigen-Negative Configurations: Ambiguous Pools—Patients with certain RHCE variant allele combinations will not express the antigen hrB, say, and may develop allo-antibodies as a result of exposure to that antigen, commonly expressed by Caucasian red cell donors. Continued transfusion support then calls for hrB- ("hrB neg") donor units. Pools comprising at least one sample lacking hrB may be identified by an "any" query, which may return a pool comprising, for example, these phenotypes:

[1] "N-s-U-c-e-hrB-hrS-VS-Lub-Jsb-k-Kpb-FyNull-Jka-Jkb-Dib-Yta-Dob-Hy-Joa-Coa"
[2] "M-N-s-U-c-e-hrB-hrS-VS-Lub-Jsb-k-Kpb-Fya-Jka-Jkb-Dib-Yta-Doa-Hy-Joa-Coa"
[3] "N-s-S-U-C-e-Lub-Jsb-k-Kpb-FyNull-Jka-Dib-Yta-Dob-Hy-Joa-Coa"
[4] "M-N-s-U-c-cE-e-E-hrS-V-VS-Lub-Jsb-k-Kpb-FyNull-Jka-Dib-Yta-Doa-Dob-Hy-Jo a-Coa"

Samples 3 and 4 lack hrB. However, to identify these samples within this "ambiguous" pool requires disambiguation, preferably by "profiling" of individual samples (d=1): by producing the complete attribute profile for each constituent sample, profiling also may "fill in" any gaps left in the partial profiles identified by sieving for a specific attribute pattern.

When constructing queries to identify pools that are ambiguous for more than a single attribute, it must be borne in mind that the specified attributes are associated with pools, NOT (necessarily) with each constituent sample. Thus, a query for pools with at least one sample having "hrB- & hrS-" may return a pool such as the one above comprising: samples 1 and 2, both expressing hrB and hrS, sample 3, expressing neither hrB nor hrS, and sample 4 expressing hrS but not hrB.

Confirmation of Homozygosity by Pooled Serology—Given a pool that is ambiguous with respect to the alleles encoding antithetical antigens, such as "e" and "E" (above), with at least one variant allele, serology may be used to confirm the presence of any homozygous sample. To that end, perform an immunoassay with a pool of cells from the sources of the DNA analyzed, and expose the cells to anti-e antibodies, labeled with a first fluorescent dye ("RED", say) and to anti-E antibodies, labeled with a second fluorescent dye ("GREEN", say). Cells from a heterozygous sample will bind both RED and GREEN antibodies, cells from homozygous samples will bind antibodies of only one color If indeed present, a true "e-" cell type will bind only the GREEN (anti-E) antibody. This immunoassay format thus conveniently distinguishes between ambiguous pool configurations reflecting the presence of heterozygotes and those reflecting the presence of at least one true homozygous variant, often the object of interest. Flow-cytometric analysis with at least two color channels, would provide convenient implementation, by gating on events comprising a single dye or both dyes. To limit profiling to pools containing homozygous variants, pools not containing true homozygous variants may be excluded from further analysis.

"Sieving" Samples for Desirable Attribute Patterns: Enrichment—African Americans display significant allelic diversity especially with respect to RHCE variants and corresponding antigen profiles. Notably, the antigens V and VS, encoded by RHCE variants RHCE*01:20, at respective abundances of 30% and 26-40%, are sufficiently common in African Americans that, when selecting a suitable African American donor for a patient lacking, say C, V and VS, or E V and VS, the candidate donor must be confirmed not to express C, V and VS or E, V and VS. While it may be tempting, in this situation, to simply rely on donors of Caucasian ethnic background who only rarely express these antigens, genetic differences with respect to other blood group antigens, notably Duffy, foreclose that option. To wit: approximately, 70% of African Americans are homozygous for the allele FY*02N:01 which silences the expression of the antigen Fyb. These individuals display the phenotype FyNull and therefore would be exposed, with near certainty, to Duffy antigens, Fyb or Fya, if given a unit from a donor of Caucasian or other non-African ethnic background. The method disclosed herein provides an effective means of accomplishing the objective of identifying suitable African American donors, by enriching the set of candidate donors selected for profiling of red blood cell antigens or their coding alleles.

Simulations of ten replicates of 96 four-sample pools, using population frequencies determined from experimental genotyping data for African Americans in the Southern United States, show the respective mean population frequencies for "V+" and "VS+" in randomly selected sets of 96 African American phenotypes, to be—33% and 40%.

Desirable donors would be (at a minimum) "V-", or "VS-" or preferably "V- & VS-". FIG. 6 summarizes outputs from simulated sieving runs, each comprising 10 replicates of 96 four-sample pools, and shows: an average of: ~38.8 samples in ~10 pools identified as unambiguous for the attribute pattern "V- & VS-"; ~8.8 samples in ~2 pools identified as unambiguous for "C- & V-& VS-"; ~10.4 samples, in ~2.5 pools identified as unambiguous for "E- & V- & VS-"; and ~15 samples in pools identified as unambiguous for "C- & V- & VS-" or "E- & V- & VS-".

Figure 8:
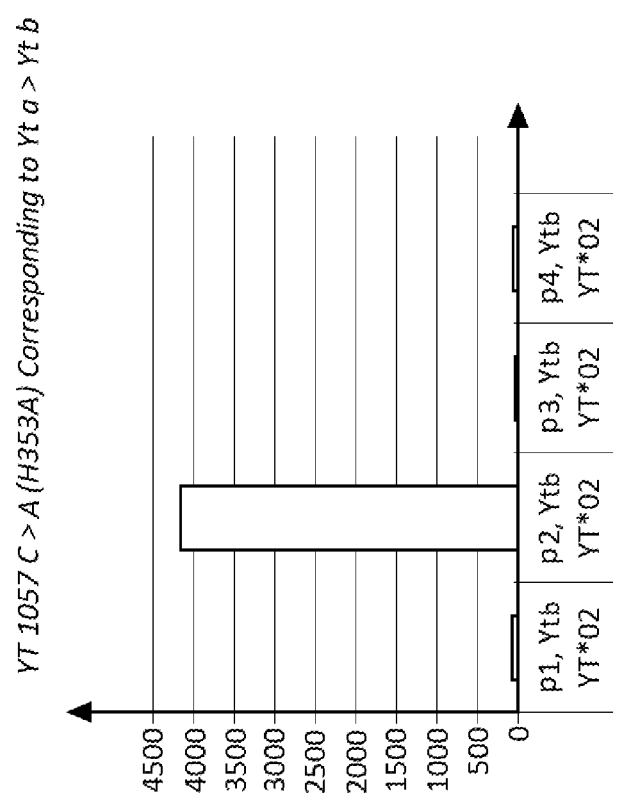
FIG. 8 is a bar graph illustrating the presence of the variant allele, YT*02, in pool "p2"; pools "p1", "p3" and "p4" are negative for the variant allele, hence homozygous and thus "unambiguous" for the normal allele, YT*01. The increase in signal intensity recorded for pool "p2" over that of the others is indicated by the increased size of the bar.

Substituting samples in these unambiguous pools for randomly selected samples, in the set to be committed to profiling will substantially enrich the profiled set for the selected attribute patterns, as illustrated in this table:

exposed to the antigen during transfusion—almost a certainty given the high incidence of the antigen they lack—may form an antibody. Such antibodies directed against a common antigen substantially complicate any subsequent transfusion support which now calls for donor units that likewise lack a common antigen. To identify such rare donor units, it is helpful to "cast a wide net" by surveying a large number of candidate units for "het" configurations, indicated by at least one variant allele such as KEL*01, LU*01, or YT*02, as illustrated in FIG. 8.

For antithetical antigens, an ambiguity implies the presence of at least one copy of the antithetical antigen. Thus, unless a pool is ambiguous for the attribute "E-", it cannot contain a sample that is homozygous for the attribute "e-", and thus an ambiguity is a necessary (but not sufficient) condition for the existence of such a sample. This will be of special interest when looking for samples that are homozygous for rare variants, such as RH-$C^X$, RH-$C^W$, Cob, Lua, Dia, DO-Joa, DO-Hy: pools that are NOT ambiguous for any of these attributes may be "de-selected" after the sieving stage. For such a search, the preferred "d" may be determined as described above, but using the probability of encountering at least one variant attribute; for example, a pool of d samples cannot contain an "e-" sample unless it contains at least one copy of "E", an event that has probability $1-(1-F_E)^d$. When the abundance is small, that probability, and the corresponding preferred "d" will be large and in practice likely limited by $d_{max}$—for example, with $d_{max}=32$, and $F_{Dia}=0.001$, setting d to $d_{max}$ would produce an expected number of $96*(1-(1-F_{Dia})^{32})=3$ ambiguous pools: only those would be candidates for further analysis.

In other cases, especially for the predominantly African American sickle cell anemia population, patients may lack

| Attribute Pattern Black Donor Population | exp nof samples in random set of 96 | exp nof samples in unambig pools | exp nof samples in enriched set of 96 | enrichment (%) | exp nof samples in enriched set of 96: 2nd pass | enrichment (%) 2nd pass |
|---|---|---|---|---|---|---|
| "V- & VS-" | 34 | 38.8 | 58 | 70.6% | 83 | 144.1% |
| "C- & V- & VS-" | 29 | 8.8 | 34 | 17.2% | 40 | 37.9% |
| "E- & V- & VS-" | 34 | 10.4 | 40 | 17.6% | 46 | 35.3% |
| "C- & V- & VS-" or "E- & V- & VS-" | 56 | 15.2 | 62 | 10.7% | 68 | 21.4% |

Thus, a single sieving pass, comprising 96 four-sample pools, will enrich a profiled set of 96 samples by an expected 17.2% for samples having the attribute pattern "C- & V- & VS-"; a second sieving pass will further increase the enrichment, as shown. An additional advantage of the method disclosed herein is this: enrichments for multiple attribute patterns may be achieved simultaneously, drawing on pools identified as unambiguous for desired attribute patterns, as well as on ambiguous pools that may contain variant alleles; the latter illustrated in the following Examples.

Figure 9:
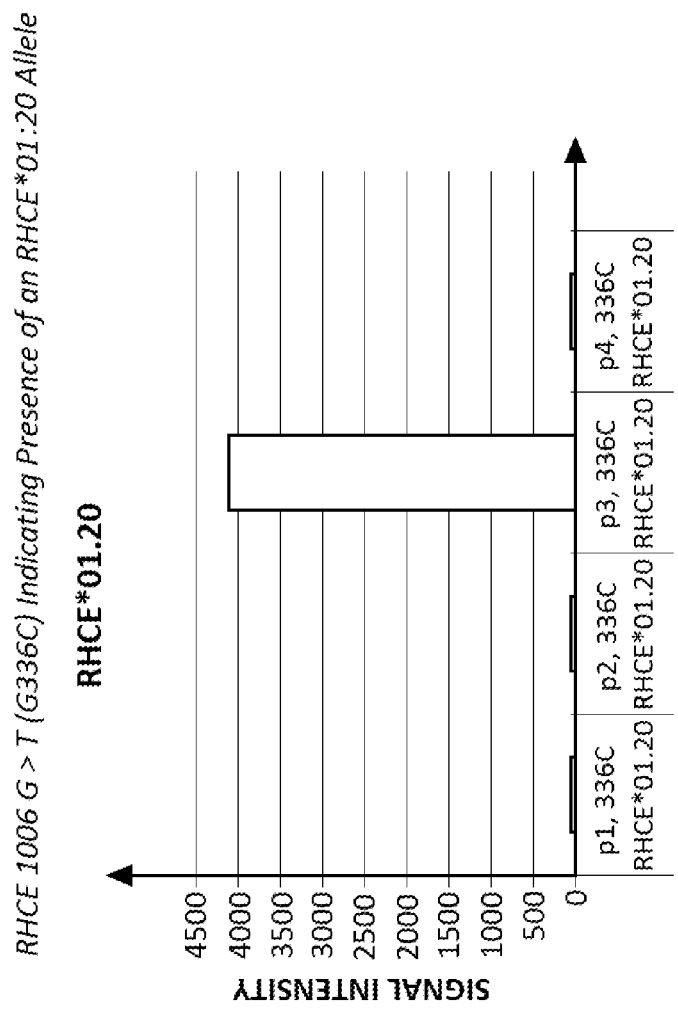
FIG. 9 is a bar graph illustrating the detection of a variant form of the Single Nucleotide Polymorphism, 1006T (corresponding to 336C), associated with the alleles RHCE*01:20:03 and RHCE*01:20:05, neither of which express the antigen V. Pool "p3" is positive for the variant form of that SNP, indicating the presence of at least one copy of one of the variant alleles, while pools "p1", "p2" and "p4" are negative for the variant, indicating expression of the V antigen by all constituent samples. The difference in signal intensity of the p3 pool is shown by the increased size of the bar.

Detecting Variant Alleles in Pooled Pools—The routine detection of variant alleles, and especially rare variant alleles, in the sieving stage, as enabled by the method disclosed here, permits the sampling of a large number of candidate samples for several rare antigen configurations, even and especially when serology reagents are not available, as in the case of many less common antigens, e.g. those in the DO or YT groups or less common antigens in the RH group, as illustrated here with reference to FIGS. 7, 8 and 9.

In rare cases, patients lacking a common (aka "high incidence") antigen such as "k" or "Yta" or "Lub", when one or both of the antigens V and VS and may also lack one or both of the antigens hrB and hrS, encoded by certain variant RHCE alleles. These antigens are expressed not only by essentially all Caucasians, but also by a substantial fraction of African Americans (see also above), so that even, or especially, when candidate units are given by African American donors, the risk of allogeneic exposure to V, VS or to hrB and hrS antigens, is significant. Accordingly, to avoid such exposure, African American donors expressing these antigens should be identified. Thus—with reference to FIG. 7—when looking for, say, candidate donors with the attribute pattern "C- & V- & hrB-", only phenotype 1 in pool "p1" and phenotype 4 in pool 2 may be suitable, though that determination requires profiling (d=1), as all pools in FIG. 7 are ambiguous for hrB-, as indicated by inspection of the allele G336C; see also FIG. 9.

Including or Excluding HLA Allele Groups—By querying pools for one or more specific single nucleotide polymorphism(s) (aka "SNP" or "SNPs") defining HLA alleles, especially if, based on population frequencies of the nucleotide observed at those specific SNP positions, these are expected to produce unambiguous pools, entire allele groups that share (or do not share) a particular nucleotide for the specific one or more SNPs may be selected ("included") or de-selected ("excluded").

For example, the SNP at position 120 in the B-locus bi-partitions the set of B-alleles into those having "B120G" and those having "B120A". For individuals of African descent, 80% of the alleles comprise the former, and 20% of the alleles the latter. The probability of encountering at least one of the less common alleles, in a pool containing d=4 samples, hence <2*4 B-alleles, is: prob(no "B120A" in pool)=$(1-f_{B-120A})^{2*d}$=0.167, yielding, an expected number of 16 (=96*prob(no "B120A" in pool)) pools not containing the variant. Accordingly, for all samples in such pools, alleles comprising "B120A", and thus all alleles in the groups B*13, B*40, B*44, B*47 are eliminated. See IPD IMGT/HLA website.

Figure 10:
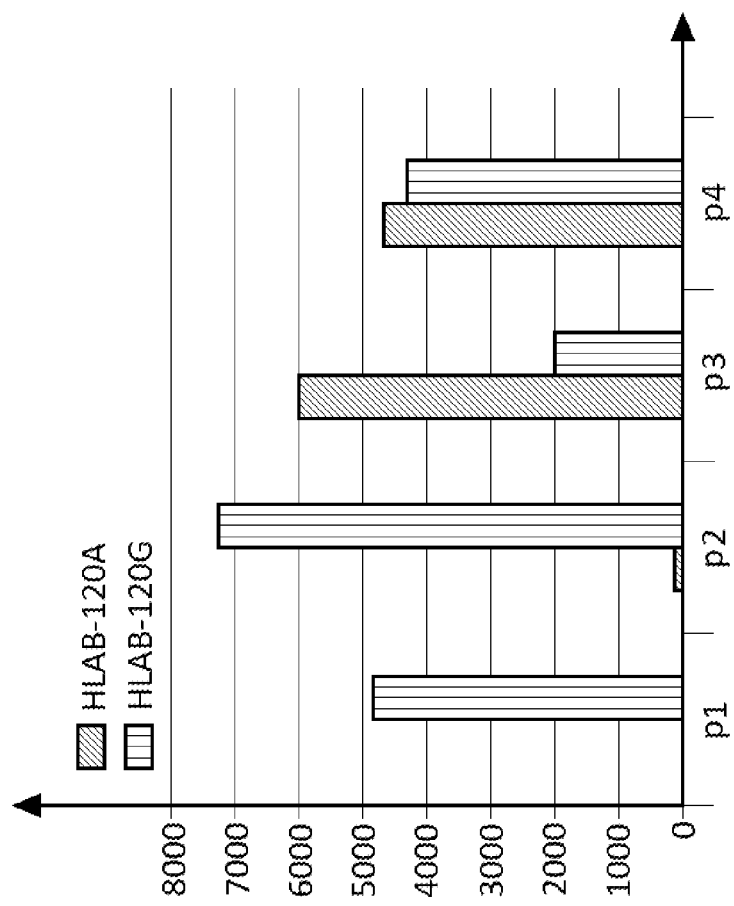
FIG. 10 is a bar graph illustrating the absence of certain HLA-B alleles comprising either "B120A" or "B120G" for four pools, each comprising four samples, with pairs of bars indicating the relative signal intensities for B120A and B120G for individual pools: no signal for "B120A" is detected in pools 1 and 2.

FIG. 10 illustrates the experimental signature of this situation: pools 1 and 2 do not produce a signal for "B120A" and thus are unambiguous for "B120G", while pools 3 and 4, produce signals for both "B120A" and "120G" and thus are ambiguous. Similar examples may be readily constructed for other variable positions, and for other loci. By "any" or "all" queries, pools may be selected for inclusion in, or exclusion from profiling. For example, given a requirement for a platelet donor with a specific HLA class I allele profile, comprising an allele in the group B*40, sieving will facilitate excluding unsuitable candidates from a large initial candidate set.

Building a Demand-Informed Population of Callable Prospective Donors of Cells—Blood centers, such as those operated by the American Red Cross and hospital transfusion services, such as those operated by many US tertiary care medical centers, as well as stem cell registries, such as the National Marrow Donor Program, in order to establish populations of callable donors of red cells, platelets and stem cells, rely on randomly recruited volunteers. Especially in connection with red cell and platelet collection, repeat donation is highly valued as they lighten the burden of donor recruitment and, to the extent that historic records of donor molecular attribute profiles are available, reduces the expense of genotyping. However, as a method for establishing a callable inventory with a desired composition of molecular attribute profiles, random sampling represents an inefficient strategy even if anticipated recipients and prospective donors were drawn from the same population—generally not a valid assumption.

The method disclosed herein enables a "directed" sampling strategy of superior efficiency in building a demand-informed callable inventory. As illustrated in the foregoing Examples, e.g. with reference to FIG. 5, the new process may be used to enrich the candidate pool for desirable attribute patterns, by selecting samples for attribute patterns that reflect historical and/or anticipated demand. In comparison to the prevailing, de facto random sampling approach to recruiting cell donors, directed sampling will be particularly efficient in identifying less common attribute patterns.

Patient Enrollment for Clinical Trials: Stratification by Molecular Attribute Profile—A key aspect of personalized (aka precision) medicine is the association between the response of individual patients to therapy and the patients' relevant genetic attributes. Of particular interest in this context are alleles comprising receptor and enzyme polymorphisms. An example of the former is the set of polymorphisms of the ADRB2 gene encoding the β2-adrenergic receptor (Hizawa2011); an example of the latter is the set of polymorphisms affecting the catalytic activity of the enzymes in the cytochrome P450 superfamily, including CYP2D6, CYP2C9 and CYP2C19 (for clinical significance and other detail, see e.g. ARUP Labs—website), with attendant effects on individual rates of metabolizing prescription drugs (See Indiana University, Dept. of Medicine, P450 drug interaction table). The determination of individual genotypes and constituent alleles therefore may inform treatment decisions, including drug and dose selection, and may also guide the design of clinical trials (Kurose2012) including the stratification of cohorts by genotype.

For example, the pooling method disclosed herein may be used to stratify patients by CYP genotype(s) of interest. Thus, to classify, by one or more CYP genotypes, Caucasian candidate participants in a drug trial for, say, angiotensin II receptor antagonists, where the CYP2C9 genotypes comprise one or both of the two principal variant alleles CYP2C9*2 and CYP2C9*3, both of which confer a reduced metabolic rate, proceed in accordance with the method disclosed herein, as follows. Select as a desired attribute pattern the absence of the alleles CYP2C9*2 (identified by the SNP 430C>T, R114C, with a frequency of ~14% in Caucasians); determine an optimal value $d_{opt}$=6, yielding 228 alleles (or 114 samples, given bi-allelic CYP genotypes) in pools unambiguous for the absence of the designated alleles, and a near-optimal, preferred value of d*=8, yielding 226 alleles (or 113 samples) in pools unambiguous for the absence of the designated alleles. Likewise, with a desired attribute pattern defined by the absence of CYP2C9*2 as well as CYP2C9*3, (SNP 1075A>C, I359L, ~6.4%), determine an optimal value $d_{opt}$=4, yielding 160 alleles (or 80 samples) in pools unambiguous for the desired attribute pattern, and a near-optimal, preferred value of d*=8, yielding 128 alleles (or 64 samples) in pools unambiguous for the desired attribute pattern.

Mutation Carrier Screening: Phasing—In like manner, the method of the present invention can be used to expand and accelerate programs of mutation carrier screening, targeting, for example, mutations associated with elevated cancer risk (e.g. BRCA-1 and BRCA-2) or autosomal recessive disorders including hemochromatosis, cystic fibrosis, β-thalassemia, sickle cell disease, lysosomal storage diseases and others. Attribute patterns of interest will comprise one or more mutant alleles: a sample with at least one mutant allele will introduce ambiguity. As the population frequencies of mutant alleles generally are in the range of at most a few percent, the method disclosed herein will call for the testing of large-d pools and thus enable large-scale screening for entire sets of mutant alleles.

Figure 11:
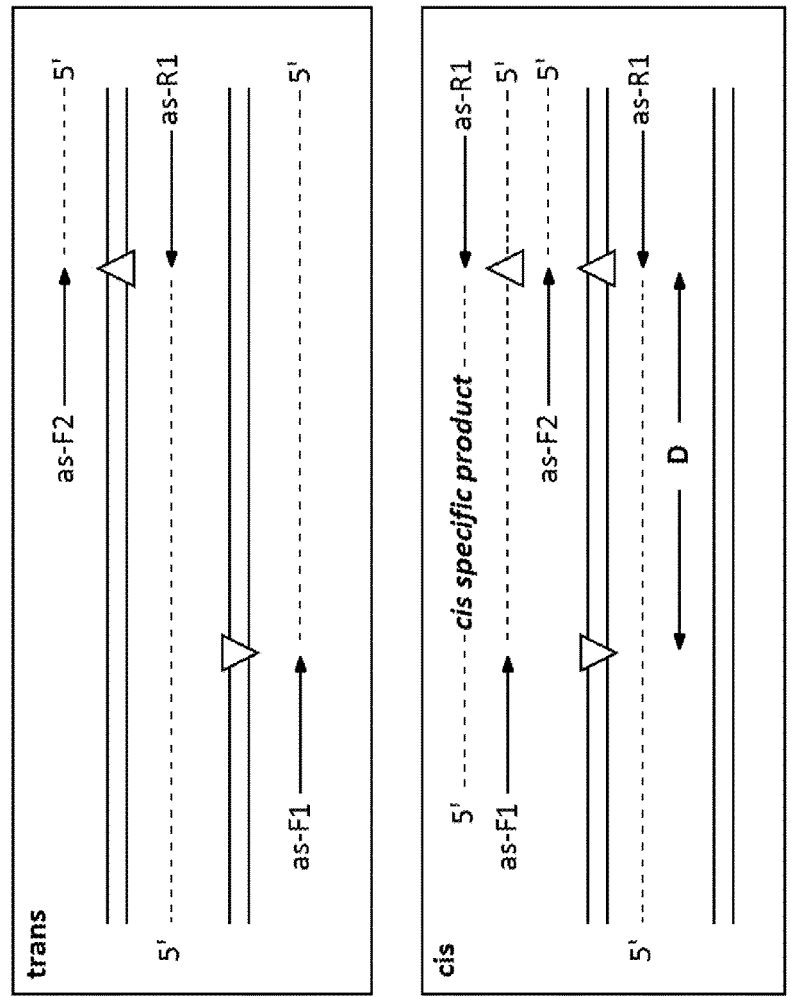
FIG. 11 is an illustration of cis- and trans-configurations of a pair mutations, showing the positions of forward and reverse primers for detecting any cis-specific product.

Of particular interest especially to recessive autosomal disorders with many causative mutations including those mentioned above is the identification not only of individuals who carry one copy, or two copies, of a mutant allele, but also patients who are heterozygous for two or more mutations, a configuration also known as "compound heterozygotic", and specifically the identification of "cis" vs "trans" configurations: in the former, a single chromosome carries two mutations ("cis") and the other remains intact, while in the latter each chromosome carries one mutation ("trans"), leaving no intact allele—is has been well recognized that this distinction has significant implications for the type and severity of clinical symptoms. The method of the invention, because it produces allele-specific products, permits the identification of cis-vs trans-configurations of mutations. Specifically, a nested PCR design comprising allele-specific primers to both mutations, and one reverse allele-specific primer to the downstream mutation generates a product, of characteristic length D, only for the cis-configuration (as depicted in FIG. 11). The presence of at least one such cis-specific product in a pool may be detected by a preferred embodiment of the method of the present invention using capillary electrophoretic analysis of attribute specific reaction products, as disclosed in U.S. application Ser. No. 14/675,981, incorporated by reference: the cis-specific product produces a peak at a specific design location, and so long as the distance, D, between the mutations exceeds a minimal length of, say, 50 nucleotides, this peak may be detected, in a pre-determined color channel, in pools or pooled pools of attribute specific reaction products.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims and their equivalents are intended to be construed to include all such embodiments and equivalent variations.

Although described in connection with preferred embodiments thereof, it will be appreciated by those skilled in the art that additions, deletions, modifications, and substitutions not specifically described may be made without departure from the spirit and scope of the invention, which is only defined in the appended claims and not elsewhere.

REFERENCES

AABB2013—"Patient Blood Management Survey Report", AABB Dec. 18, 2015.

Castro2002—Castro O, Sandler S G, Houston-Yu P, Rana S "Predicting the effect of transfusing only phenotype-matched RBCs to patients with sickle cell disease: theoretical and practical implications", Transfusion 2002 June; 42(6):684-90.

Chou2013—Chou S T, Jackson T, Vege S, Smith-Whitley K, Friedman D F & Westhoff C M "High prevalence of red cell alloimmunization in sickle cell disease despite transfusion from Rh-matched minority donors", Blood 2013 August; 122(6): 1062-1071.

Doehner2010—Doehner H, Estey E H, Amadori S, Appelbaum F R, Buechner T, Burnett A K et al "Diagnosis and management of acute myeloid leukemia in adults", Blood 2010; 115:453 474.

Hashmi2005—Hashmi G, Shariff T, Seul M, Vissavajjhala P, Hue-Roye K, Charles-Pierre D, et al. "A flexible array format for large-scale, rapid blood group DNA typing", Transfusion. 2005 May; 45(5):680-8.

Hashmi2007—Hashmi G[1], Shariff T, Zhang Y, Cristobal J, Chau C, Seul M, et al., "Determination of 24 minor red blood cell antigens for more than 2000 blood donors by high-throughput DNA analysis", Transfusion. 2007 April; 47(4):736-47.

Hizawa2011—Hizawa N, "Pharmacogenetics of β2 agonists", Allergology International. 2011; 60:239-246

Kurose2012—Kurose K, Sugiyama E & Saito Y, "Population Differences in Major Polymorphisms of Pharmacokinetics/Pharmacodynamics-related Genes in Eastern Asians and Europeans", Drug Metab. Pharmakokinet. 2012; 27(1): 9-54.

Lee2006—Lee M T, Piomelli S, Granger S S, Miller S T, Harkness S, Brambilla D J et al. "Stroke Prevention Trial in Sickle Cell Anemia (STOP): extended follow-up and final results", Blood. 2006 Aug. 1; 108(3): 847-852.

Meehan2000—Meehan K R, Matias C O, Rathore S S, Sandler S G, Kallich J, LaBrecque J et al. "Platelet Transfusions: Utilization and Associated Costs in a Tertiary Care Hospital", Am J Hematology 2000; 64: 251-256.

Moulds2011—"BeadChip Molecular Immunohematology", Moulds J M, Ness P M & Sloan S R, Eds, Springer Verlag, New York, 2011.

Pham2011—Pham B N, Peyrard T, Juszczak G, Beolet M, Deram G, Martin-Blanc S, Dubeaux I, Roussel M, Kappler-Gratias S, Gien D, Poupel S, Rouger P, Le Pennec P Y, "Analysis of RhCE variants among 806 individuals in France: considerations for transfusion safety, with emphasis on patients with sickle cell disease", Transfusion. 2011 June; 51(6):1249-60.

Reid2004—Reid M & Lomas Francis C, "The Blood Group Antigen Factsbook", 2nd Ed, Elsevier 2004

TRAP1997—TRAP Study Group. Leukocyte reduction and ultraviolet B irradiation of platelets to prevent alloimmunization and refractoriness to platelet transfusions. The Trial to Reduce Alloimmunization to Platelets Study Group. New Engl J Med 1997; 337(26):1861-69.

Wayne2000—Wayne A S, Schoenike S E, Pegelow C H, "Financial analysis of chronic transfusion for stroke prevention in sickle cell disease", Blood 2000; 96(7): 2369—2372 (2000).

What is claimed is:

1. A process of identifying biological samples with particular desired attributes and selecting them, the process comprising the pooling of different biological samples wherein each of the desired attributes can be determined by a method capable of detecting, for a particular pool of samples, either the presence of desired attributes in at least one of the samples, but not all of the samples in that pool, or their presence or absence in all of the samples in that pool, the process further comprising:

determining, based on at least two desired attributes, the quantity "d" which is the preferred number of samples per pool, by selecting a positive integer value as "d" which produces the maximum or a value near the maximum of the product of: d times the number of expected sample pools whose constituent samples all have, or do not have, the desired attributes, based on the expected frequencies of the desired attributes in the population from which samples are drawn;

dividing the plurality of samples into subsets, comprising approximately "d" samples per subset, such that each of the plurality of samples is included in at least one subset, and forming unique pools with aliquots from different sample subsets;

forming, for each pool, attribute-specific, source-tagged reaction products each having a source tag identifying the pool and a marker-tag identifying a particular desired attribute;

identifying unambiguous pools wherein all samples in said unambiguous pools have the desired attribute or no sample does, or identifying ambiguous pools wherein at least one constituent sample, but not all constituent samples, has the desired attribute; and performing at least one of the following:
(i) identifying and selecting samples from unambiguous pools for the desired attribute and either leaving additional attributes in their attribute profiles undetermined, or further analyzing the selected samples; or (ii) identifying and selecting samples from ambiguous pools and further analyzing the samples.

2. The process of claim 1 wherein the further analyzing of samples selected from the unambiguous pools or from the ambiguous pools determines attributes other than the desired attribute.

3. The process of claim 1 wherein, in a first reaction, source-tagged reaction products are formed which include a site capable of being interrogated for the purpose of identifying the desired attribute, and wherein, in a second reaction, attribute-specific source-tagged reaction products are formed, each such attribute-specific source-tagged reaction products comprising a combination of source-tag and marker-tag.

4. The process of claim 1 wherein the further analyzing of samples selected from unambiguous pools with one or more attributes left undetermined produces their attribute profiles for all desired attributes.

5. The process of claim 1 wherein the constituent samples from ambiguous pools are further analyzed individually to resolve which samples have, and which do not have, the desired attribute.

6. The process of claim 1 wherein selected samples with desired attributes also have attributes left undetermined, and wherein these attributes are ignored when selecting samples.

7. The process of claim 6 wherein the desired attribute is the presence or absence of an antigen having an antithetical antigen and wherein for constituent samples of a pool that is ambiguous with respect to the antithetical antigens, the presence of at least one sample that has, or does not have, the antigen in the pair of antithetical antigens confirmed by an assay wherein a first antibody labeled with a first color is directed to a first antithetical antigens, and a second antibody labeled with a second color is directed to a different antithetical antigen, to determine the presence or absence, in the pool, of samples expressing only one antithetical antigen or both antithetical antigens.

8. The process of claim 7 wherein the ambiguous pools include samples with both antithetical antigens which are ignored in selecting samples.

9. The process of claim 1 wherein a sample can be homozygous or heterozygous for the alleles encoding the desired attribute.

10. The process of claim 1 wherein the value selected as "d" is greater than that yielding the maximum of the product of: d times the number of expected unambiguous sample pools, so as to enlarge the total number of samples included.

11. The process of claim 1 wherein if d is greater than a preset maximum value, dmax, then reducing d to that value.

12. The process of claim 11, wherein dmax is determined by practical limitations of the method invoked to detect attributes such that desired attributes can be readily detected in a pool with d samples in it so long as d does not exceed dmax.

13. A method of selecting biological samples, from a set of candidate samples, in accordance with a pattern of desired attributes wherein sample pools of different samples are formed and each attribute in the attribute pattern can be determined by a method capable of detecting, for a particular pool of samples, either the presence of desired attributes in at least one of the samples, but not all of the samples in that pool, or the presence or absence of the desired attributes in all samples in that pool, the process comprising:
 determining, based on the desired attributes, the quantity "d" which is the preferred number of samples per pool by selecting as "d" a positive integer value which, based on the expected frequencies of the desired attributes in the population from which samples are drawn, produces the maximum or a value near the maximum of the expected number of samples in pools whose constituent samples all have, or all do not have, the desired attributes; dividing the plurality of samples into subsets, comprising approximately "d" samples per subset such that each of the plurality of samples is included in at least one subset, and, forming unique pools with aliquots from different sample subsets;
 forming, for each pool, attribute-specific, source-tagged reaction products each having a source tag identifying the pool and a marker-tag identifying a particular desired attribute;
 identifying unambiguous pools wherein samples in said unambiguous pools all have, or all do not have, the desired attributes, or identifying ambiguous pools wherein at least one constituent sample, but not all constituent samples, does not have the desired attributes;
 identifying and selecting samples from unambiguous pools for the desired attributes;
 optionally either leaving additional attributes in their attribute profiles undetermined, or further analyzing the selected samples; and
 optionally further analyzing the constituent samples from ambiguous pools to resolve which have and which do not have the desired attributes in the pattern.

14. The method of claim 13 wherein the attribute pattern reflects the allele or antigen profiles of transfusion-dependent patients.

15. The method of claim 13 wherein the constituent samples from the ambiguous pools are further analyzed individually to determine the presence of attributes other than desired attributes.

16. The method of claim 13 wherein selected samples with the desired attributes also have unknown attributes which are left undetermined and wherein these attributes are ignored when selecting samples.

17. A method of enriching a sample set for desired attributes by identifying samples in pools of samples that are ambiguous for said attributes; the process comprising pooling of different biological samples and wherein each of said attributes can be determined by a method capable of detecting, for a particular pool of samples, either the presence of the desired attributes in at least one of the samples in that pool, or the presence or absence of the desired attributes in all samples in that pool, the process comprising:
 determining, based on all the attributes, the quantity "d" which is the preferred number of samples per pool by selecting a positive integer value as "d" which produces the maximum or a value near the maximum of the product of: d times the number of expected sample pools whose constituent samples all have, or do not have, the desired attributes, based on the expected frequencies of the desired attributes in the population from which samples are drawn;
 dividing the plurality of samples into subsets, comprising approximately d samples per subset such that each of the plurality of samples is included in at least one subset, and, forming unique pools with aliquots from different sample subsets;
 forming, for each pool, attribute-specific, source-tagged reaction products each having a source tag identifying the pool and a marker-tag identifying a particular desired attribute;

identifying ambiguous pools wherein at least one, but not all samples in said ambiguous pools have the desired attributes; and identifying and selecting samples from the ambiguous pools for further analysis.

18. The method of claim 17 wherein selected samples with desired attributes also have attributes left undetermined, and wherein these attributes are ignored when selecting samples.

19. The method of claim 17 wherein the desired attributes are antithetical antigens and wherein for constituent samples of a pool that is ambiguous with respect to antithetical antigens, the presence of at least one sample that is homozygous for a desired antigen is confirmed by an assay wherein a first antibody labeled with a first color is directed to a first of the antithetical antigens, and a second antibody labeled with a second color is directed to a second of the antithetical antigens, to determine the presence or absence, in the pool, of samples expressing both antithetical antigens.

20. The method of claim 19 wherein the ambiguous pools include samples with both antithetical antigens which are ignored in selecting samples.

21. The process of claim 5 further including deselecting or discarding samples from the ambiguous pools.

22. The method of claim 13 further including de-selecting or discarding samples from the ambiguous pools.

23. The method of claim 17 further including de-selecting or discarding samples from the ambiguous pools.

\* \* \* \* \*